(12) United States Patent
Sandrin et al.

(10) Patent No.: US 9,636,085 B2
(45) Date of Patent: May 2, 2017

(54) METHOD FOR DETERMINING, IN REAL TIME, THE PROBABILITY THAT TARGET BIOLOGICAL TISSUE IS OPPOSITE AN ULTRASONIC TRANSDUCER

(75) Inventors: Laurent Sandrin, L'Hay les Roses (FR); Véronique Miette, Villejuif (FR); Jennifer Oudry, Malakoff (FR); Stéphane Audiere, Villejuif (FR); Yassine Mofid, Saint Avertin (FR)

(73) Assignee: ECHOSENS, Paris (FR)

( * ) Notice: Subject to any disclaimer, the term of this patent is extended or adjusted under 35 U.S.C. 154(b) by 570 days.

(21) Appl. No.: 14/236,588

(22) PCT Filed: Jul. 26, 2012

(86) PCT No.: PCT/EP2012/064738
§ 371 (c)(1),
(2), (4) Date: Mar. 24, 2014

(87) PCT Pub. No.: WO2013/017532
PCT Pub. Date: Feb. 7, 2013

(65) Prior Publication Data
US 2014/0249415 A1    Sep. 4, 2014

(30) Foreign Application Priority Data

Aug. 3, 2011 (FR) .................................. 11 57119

(51) Int. Cl.
*A61B 8/08* (2006.01)
*A61B 8/00* (2006.01)
(52) U.S. Cl.
CPC .............. *A61B 8/5223* (2013.01); *A61B 8/08* (2013.01); *A61B 8/085* (2013.01); *A61B 8/0858* (2013.01); *A61B 8/4483* (2013.01); *A61B 8/461* (2013.01); *A61B 8/5207* (2013.01)

(58) Field of Classification Search
None
See application file for complete search history.

(56) References Cited

PUBLICATIONS

Pauly H., et al., "Mechanism of absorption of ultrasound in liver tissue," J. Acoust. Soc. Am., 1971, 50(2B), pp. 692-699.
(Continued)

*Primary Examiner* — Long V Le
*Assistant Examiner* — Bradley Impink
(74) *Attorney, Agent, or Firm* — Pillsbury Winthrop Shaw Pittman LLP (57) ABSTRACT

A method for determining, in real time, the probability that target biological tissue is opposite an ultrasonic transducer, the method including: transmitting, via an ultrasonic transducer, an ultrasonic signal into biological tissue; the ultrasonic transducer receiving the transmitted ultrasonic signal which has been backscattered by the biological tissue; calculating at least two instantaneous parameters of the backscattered ultrasonic signal; calculating a predictive value of the presence of an acoustic signature of target biological tissue, the predictive value being calculated via a statistical law using the at least two calculated instantaneous parameters; estimating the probability that the target biological tissue is opposite the ultrasonic transducer, the estimation depending on the calculated predictive value and/or on at least one strength condition based on at least one of the two calculated instantaneous parameters.

17 Claims, 3 Drawing Sheets

(56) References Cited

PUBLICATIONS

Schmitz, G., et al., "Tissue Characterization of the Prostate using Kohonen-Maps," Ultrasonics Symposium, 1994, pp. 1487-1490.

Scheipers, U., et al., "Ultrasonic Multifeature Tissue Characterization for Prostate Diagnostics," Ultrasound in Medicine and Biology, Aug. 2003, 2 pages.

Kadah, Y.M., et al., "Classification Algorithms for Quantitative Tissue Characterization of Diffuse Liver Disease from Ultrasound Images," IEEE Transactions on Medical Imaging, vol. 15, No. 4, Aug. 1996, pp. 466-478.

Chou, Y.-H., et al., "Stepwise Logistic Regression Analysis of Tumor Contour Features for Breast Ultrasound Diagnosis," Ultrasound in Medicine and Biology, November, vol. 27. No. 11, 2001, pp. 1493-1498.

International Search Report as issued for International Application No. PCT/EP2012/064738, dated Sep. 21, 2012.

METHOD FOR DETERMINING, IN REAL TIME, THE PROBABILITY THAT TARGET BIOLOGICAL TISSUE IS OPPOSITE AN ULTRASONIC TRANSDUCER

CROSS REFERENCE TO RELATED APPLICATIONS

This application is the U.S. National Stage of PCT/EP2012/064738, filed Jul. 26, 2012, which in turn claims priority to French Patent Application No. 1157119, filed Aug. 3, 2011, the entire contents of all applications are incorporated herein by reference in their entireties.

The invention relates to a method for determining, in real time, the probability that target biological tissue is opposite an ultrasonic transducer. The ultrasonic transducer may, for example, belong to a so-called "blind" or "partially blind" measurement probe. "Blind" is taken to mean that the measurement device to which the measurement probe is connected is not provided with a real time imaging mode. Moreover, "partially blind" is taken to mean that the imaging mode of the measuring device is limited to a one-dimensional (1D) ultrasonic line of A-SCAN type optionally associated with a type M mode.

Conventionally, to measure quantitative or qualitative parameters of biological tissue, a measurement probe is positioned opposite said tissue.

When it is wished to position a blind or partially blind measurement probe opposite target biological tissue, the positioning may be carried out in two ways:
  positioning without resorting to an ancillary imaging probe, such positioning making it necessary for the operator to have knowledge of human or animal anatomy.
  positioning by means of an imaging probe, for example an echography probe, different to the measurement probe.
  Such implementations lead however to drawbacks.

In fact, the use of a blind measurement probe without resorting to an imaging probe does not make it possible to ensure with certainty that the measurement probe is positioned opposite the target biological tissue that it is wished to measure. The positioning of the measurement probe is carried out approximately, since anatomic knowledge is averaged over the general population. Thus, the anatomy of the individual on whom it is wished to measure parameters has to conform to the standard. In fact, if the anatomy of the individual is different to the average, the measurement probe will not be positioned opposite the target biological tissue and the measurement obtained will not be representative of the target biological tissue.

Furthermore, the use of an imaging probe so as to facilitate the positioning of the measurement probe opposite the target biological tissue imposes, firstly, pinpointing the target biological tissue by means of the imaging probe then, secondly, once the target biological tissue has been pinpointed, removing said imaging probe to replace it with a measurement probe. Nevertheless, this replacement of the imaging probe by the measurement probe does not make it possible to ensure with certainty that the measurement probe is positioned opposite the target biological tissue since the biological tissues of an individual are subject to movements, for example of respiratory type.

An additional possibility for carrying out a quantitative or qualitative measurement of biological tissue is to use a probe capable of imaging and capable of measuring biological tissues. To interpret the image obtained using this probe, it is necessary that the operator has enhanced knowledge, on the one hand, in the field of human or animal medicine and, on the other hand, in the field of medical imaging.

Moreover, an operator having such knowledge may nevertheless make errors in interpretation of the image used for the positioning of the probe.

The aim of the method of the invention is thus particularly to overcome the drawbacks of the prior art. In this context, the invention aims to propose a method for determining the probability that target biological tissue is opposite an ultrasonic transducer not requiring, for the operator, enhanced knowledge in the field of human or animal medicine or in the field of medical instrumentation and moreover avoiding an error of the operator.

To this end, the invention relates to a method for determining, in real time, the probability that target biological tissue is opposite an ultrasonic transducer, said method comprising the following steps:
  transmitting, via an ultrasonic transducer, at least one ultrasonic signal into biological tissue;
  receiving, via said ultrasonic transducer, at least one transmitted ultrasonic signal which is backscattered by said biological tissue;
  calculating at least two instantaneous parameters of said at least one backscattered ultrasonic signal;
  calculating a predictive value of the presence of an acoustic signature of target biological tissue, said predictive value being calculated via a statistical law using said at least two calculated instantaneous parameters;
  estimating the probability that said target biological tissue is opposite said ultrasonic transducer, said estimation depending on said calculated predictive value and/or at least one strength condition based on at least one of said two calculated instantaneous parameters.

It should be noted that the ultrasonic transducer used by the method may be of single element or multi element type.

A single element ultrasonic transducer can transmit and receive a single ultrasonic signal whereas a multi element ultrasonic transducer can transmit and receive a plurality of ultrasonic signals simultaneously.

Thanks to the method of the invention, one estimates, in real time, the probability that an ultrasonic transducer is opposite target biological tissue. This estimation is carried out automatically and does not require any competence or any interpretation of the operator implementing the ultrasonic transducer. The estimation may be returned to the operator in the form of a so-called sensorial indication (visual, audible, tactile (vibration), etc.) or instead directly used to trigger a measurement automatically.

The method according to the invention may also have one or more of the characteristics below, considered individually or according to any technically possible combinations thereof.

In a non-limiting implementation of the method according to the invention, the calculation of a predictive value is carried out via said at least two calculated instantaneous parameters and calculated instantaneous parameters memorised earlier.

In a non-limiting implementation of the method according to the invention, the estimation depending on the calculated predictive value is carried out by comparing the calculated predictive value to a single or several determined prediction threshold values such that:
  when the calculated predictive value is compared to a single determined maximum prediction threshold value, if the calculated predictive value is strictly less than the determined maximum prediction threshold value then the ultrasonic transducer is opposite the target biological tissue, if the calculated predictive value is greater than or equal to the determined maximum prediction threshold value, then the ultrasonic transducer is opposite biological tissue different to the target biological tissue;

when the calculated predictive value is compared to a determined maximum prediction threshold value and a determined minimum prediction threshold value, if the calculated predictive value is less than or equal to the determined minimum prediction threshold value then the ultrasonic transducer is opposite the target biological tissue, if the calculated predictive value is greater than or equal to the determined maximum prediction threshold value, then the ultrasonic transducer is opposite biological tissue different to the target biological tissue, if the calculated predictive value is strictly greater than the determined minimum prediction threshold value and strictly less than the determined maximum prediction threshold value then the ultrasonic transducer is assumed to be opposite the target biological tissue. This uncertainty may correspond to an acoustic signature of the target biological tissue modified by the presence of heterogeneities caused by metastases or instead by the presence of blood vessels, etc.

In a non-limiting implementation of the method according to the invention, the at least two calculated instantaneous parameters are chosen from the following parameters:

the energy of the at least one backscattered ultrasonic signal, the attenuation of the at least one backscattered ultrasonic signal, the linearity of the envelope of the at least one backscattered ultrasonic signal, the coefficient of inter-correlation of the backscattered ultrasound signals received at two successive moments, the amplitude or the maximum variations of amplitude of the envelope of the backscattered ultrasonic signal, the correlation of the at least one backscattered ultrasonic signal, the spectral variance of the at least one backscattered ultrasonic signal, the backscattering coefficient of the at least one backscattered ultrasonic signal.

In a non-limiting implementation of the method according to the invention, the strength condition is:

if the linearity of the envelope of the at least one calculated backscattered ultrasonic signal is greater than or equal to a determined linearity threshold value, then the ultrasonic transducer is opposite the target biological tissue, and/or if the energy of the at least one backscattered ultrasonic signal is greater than or equal to a determined threshold energy value, then the ultrasonic transducer is opposite the target biological tissue.

In a non-limiting implementation of the method according to the invention, whatever the calculated predictive value, said strength condition is:

if the linearity of the envelope of the at least one calculated backscattered ultrasonic signal is strictly less than the determined linearity threshold value, then the ultrasonic transducer is opposite biological tissue different to the target biological tissue, if the energy of the at least one backscattered ultrasonic signal is strictly less than the determined threshold energy value, then the ultrasonic transducer is opposite biological tissue different to the target biological tissue.

In a non-limiting implementation of the method according to the invention, the statistical law is a logistic regression such that the predictive value is calculated via the following logistic regression:

$$P=\beta_0+\beta_1 \cdot \text{Parameter\_calculated\_1}+ \ldots +\beta_n \cdot \text{Parameter\_calculated\_}n$$

In a non-limiting implementation of the method according to the invention, the method comprises an additional step of indicating, in real time, the probability that the target biological tissue is opposite the ultrasonic transducer. The indication may be a visual, and/or audible and/or tactile indication. In a non-limiting implementation of the method according to the invention, visual indication is achieved by the display of a colour gradient. Preferentially, the colour gradient follows an S-shaped curve.

In a non-limiting implementation of the method according to the invention, when the ultrasonic transducer is opposite the target biological tissue, a quantitative and/or qualitative measurement of the target biological tissue is triggered automatically or manually. Preferentially, the measurement is carried out over a determined depth dependent on the frequency of the at least one transmitted ultrasonic signal. For example, this determined depth may be comprised between 10 and 90 mm or between 35 and 75 mm for an ultrasonic signal of 2.5 Mhz, the determined depth being measured from the contact surface between the ultrasonic transducer and the biological tissue in contact.

In a non-limiting implementation of the method according to the invention, the method comprises an additional step of validation of the quantitative and/or qualitative measurement. This validation may for example be carried out by means of the predictive value of the presence of the target biological tissue.

The invention also relates to a device for determining, in real time, the probability that target biological tissue is opposite an ultrasonic transducer, the device comprising at least one ultrasonic transducer capable of transmitting and receiving ultrasound signals, the device being capable of:

emitting, via the ultrasonic transducer, at least one ultrasound signal into biological tissue;

receiving, via the ultrasonic transducer, the at least one transmitted ultrasonic signal which is backscattered by the biological tissue;

calculating at least two instantaneous parameters of the at least one b ackscattered ultrasonic signal;

calculating a predictive value of the presence of an acoustic signature of the target biological tissue, the predictive value being calculated via a statistical law using the at least two calculated instantaneous parameters;

estimating the probability that the target biological tissue is opposite the ultrasonic transducer, the estimation depending on the predictive value and/or on at least one strength condition based on at least one of the two calculated parameters, indicating, via an indicator, in real time the probability that the target biological tissue is opposite the ultrasonic transducer.

Other characteristics and advantages of the invention will become clear from the description that is given hereafter, as an indication and in no way limiting, with reference to the appended figures, among which.

For reasons of clarity, only elements essential for the understanding of the invention have been represented, without respect for scale and in a schematic manner.

Figure 1:
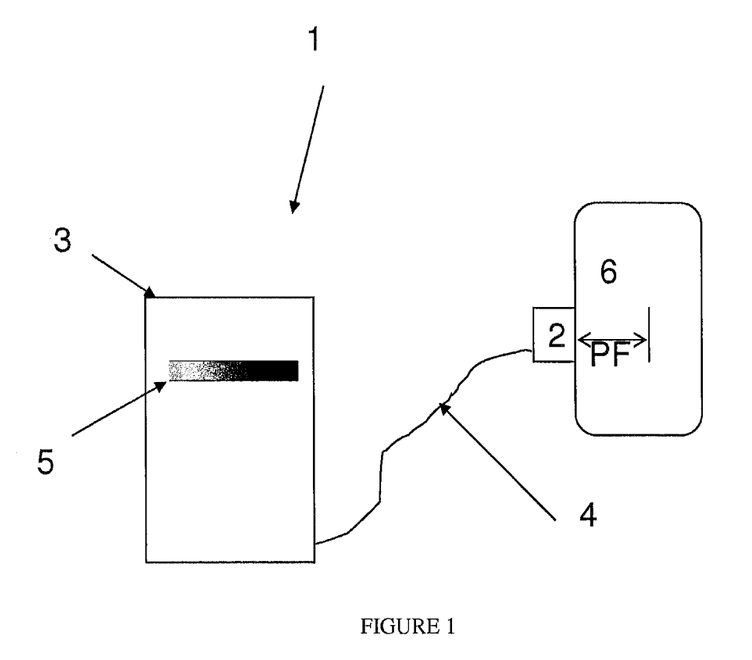
FIG. 1 illustrates in a schematic manner a device for determining, in real time, the probability that target biological tissue is opposite an ultrasonic transducer according to the invention.

A device 1 for determining, in real time, the probability that target biological tissue is opposite an ultrasonic transducer according to the invention is represented in FIG. 1. The device 1 in particular comprises an ultrasonic transducer 2 connected to an information processing unit 3 by a wire link 4. The device 1 further comprises an indicator 5, in real time, of the probability that target biological tissue is opposite the ultrasonic transducer 2. The operation of this device 1 will be detailed hereafter.

In the non-limiting example described, the ultrasonic transducer 2 used is a single element transducer. Thus, in such an embodiment, the single element ultrasonic transducer 2 may uniquely transmit and receive one ultrasonic signal at the same time.

Figure 2:
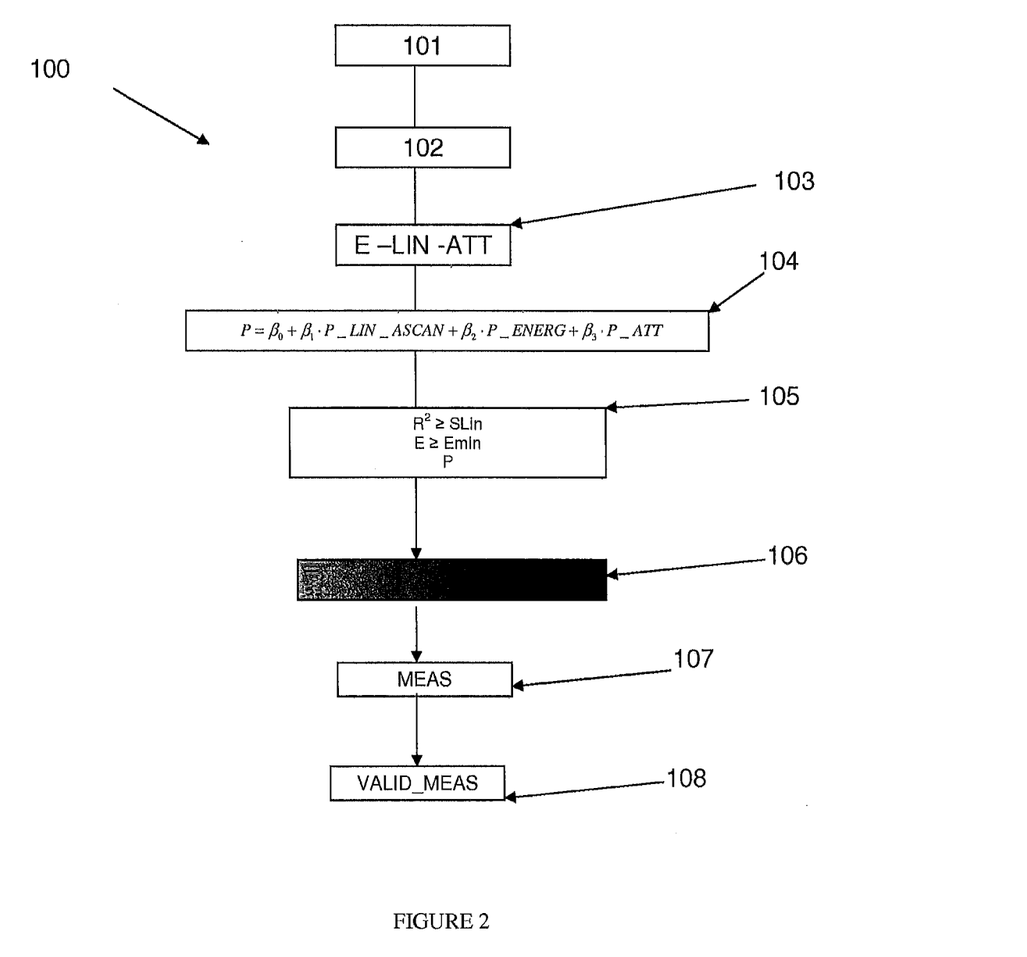
FIG. 2 represents a synoptic of the steps of a method for determining, in real time, the probability that target biological tissue is opposite an ultrasonic transducer according to the invention.
Figure 3:
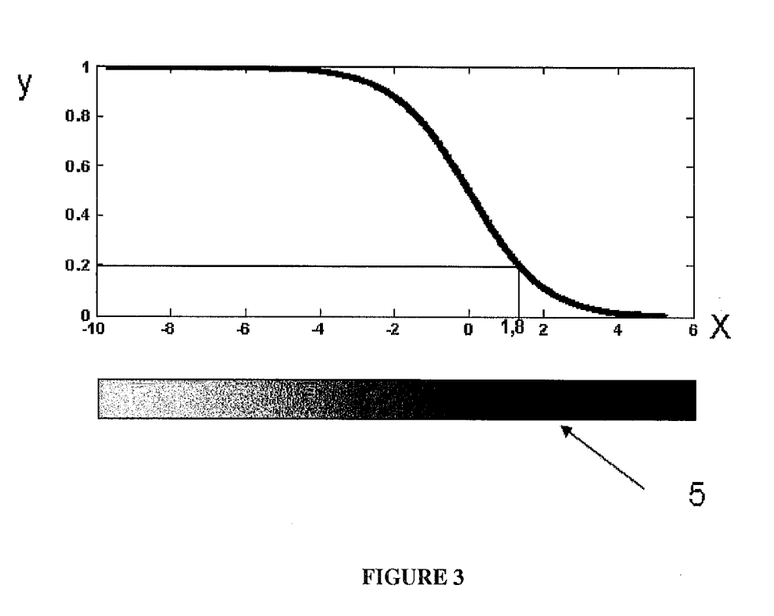
FIG. 3 illustrates a step of visual indication implemented by a method according to the invention.

The steps of the method 100 for determining, in real time, the probability that target biological tissue is opposite an ultrasonic transducer are particularly described in support of FIGS. 1 to 3.

In a non-limiting example of implementation of a method 100 according to the invention, the target biological tissue is the hepatic parenchyma. Thus, prior to the implementation of the method 100, the ultrasonic transducer 2 is positioned approximately opposite the hepatic parenchyma 6.

In a first step, as soon as the ultrasonic transducer 2 is approximately positioned, a transmission 101 is triggered via the ultrasonic transducer 2, an ultrasonic signal in the biological tissue 15 situated opposite the ultrasonic transducer 2. The transmitting frequency of this ultrasonic transducer 2 may for example be 2.5 MHz.

In a second step, the transmitted ultrasonic signal backscattered by the biological tissue situated opposite the ultrasonic transducer 2 is received (102) by the ultrasonic transducer 2.

In a third step, a calculation 103 of at least two instantaneous parameters of the backscattered ultrasonic signal received during the receiving step 102 is carried out.

In a non-limiting example, two of the following three parameters are calculated 103:
the energy E of the backscattered ultrasonic signal,
the attenuation ATT of the backscattered ultrasonic signal,
the linearity LIN of the envelope of the backscattered ultrasonic signal,
the inter-correlation coefficient of the backscattered ultrasound signals received at two successive moments,
the amplitude or the maximum variations of amplitude of the envelope of the backscattered ultrasonic signal,
the correlation of the at least one backscattered ultrasonic signal,
the spectral variance of the at least one backscattered ultrasonic signal,
the backscattering coefficient of the at least one backscattered ultrasonic signal.

It is understood that the aforementioned calculated parameters are non-limiting. Thus, other parameters may be calculated.

In an advantageous non-limiting example, the following three parameters are calculated 103:
the energy E of the backscattered ultrasonic signal,
the attenuation ATT of the backscattered ultrasonic signal, and
the linearity LIN of the envelope of the backscattered ultrasonic signal.

It should be noted that the choice of the three parameters is not limited to those mentioned above, namely the energy E, the attenuation ATT and the linearity LIN of the envelope of the backscattered ultrasonic signal.

The parameter of the energy E of the ultrasonic signal.

In a non-limiting example, the parameter of the energy E of the backscattered ultrasonic signal corresponding to the square of the amplitude of the backscattered ultrasonic signal (also designated by the acronym IBS for Integrated BackScatter) may be calculated by means of the following formula:

$$IBS = \sum_{Zmin}^{Zmax} \text{Signal}(z)^2$$

With:
z=vt/2, where v is the velocity of the ultrasounds in the medium and t the time taken by the ultrasonic signal to cover the distance z, signal=amplitude of the backscattered ultrasonic signal.

The parameter of the attenuation ATT of the backscattered ultrasonic signal.

In a non-limiting example, the parameter of the attenuation ATT of the backscattered ultrasonic signal is calculated by means of the following formula:

$$ATT(f,z) = e^{\alpha(f)z}$$

In which, the coefficient $\alpha(f)$ is calculated by means of the following formula:

$$\alpha(f) = \frac{1}{e} \ln \frac{P_1(f)}{P_2(f)}$$

$$Np \cdot m^{-1}$$

With:
e=thickness of the biological tissue through which a transmitted ultrasonic signal passes,
$P_1$=energy of the transmitted ultrasonic signal, and
$P_2$=energy of the ultrasonic signal after having passed through the measurement thickness e of the biological tissue.

Moreover, in the document (Pauly H, Schwan P., *Mechanism of absorption of ultrasound in liver tissue*. J. Acoust. Soc. Am., 1971. 50(2B), pp. 692-699), it has been demonstrated that the attenuation ATT of the backscattered ultrasonic signal decreases quasi-linearly with frequency. In other words, in the ultrasonics field, an attenuation measurement defines the calculation of the attenuation slope expressed in $dB \cdot cm^{-1} \cdot MHz^{-1}$. Thus, in another non-limiting example, the attenuation ATT of the backscattered ultrasonic signal is calculated via the following formula:

$$ATT = \alpha(f) = \alpha_0 + \beta(f - f_c) \; dB \cdot cm^{-1}$$

With
$\beta(dB \cdot cm^{-1} \cdot MHz^{-1})$=the attenuation slope as a function of the transmitting frequency of the ultrasonic transducer,
f=the transmitting frequency of the ultrasonic transducer,
fc=the central frequency of the ultrasonic transducer, and
$\alpha_0(dB \cdot cm^{-1})$=the attenuation at the central frequency fc.

In a non-limiting example, the coefficients $\alpha_0$ and $\beta$ are predetermined in an empirical manner.

The linearity LIN of the envelope of the backscattered ultrasonic signal.

The linearity LIN of the envelope of the backscattered ultrasonic signal is efficient for detecting an interface in a linearly attenuated signal.

In a non-limiting example applied to the liver, in a homogeneous medium the A-SCAN, which represents the logarithm of the envelope of the backscattered ultrasonic signal, has a linear component. This component is the value of the attenuation in the temporal domain. The linearity LIN of the envelope of the backscattered ultrasonic signal may for example be used to detect an interface formed by blood vessels or by the wall of intestines. The detection of the wall of intestines results in a more or less wide peak on the A-SCAN. In both cases, the linearity of the A-SCAN is no longer respected.

The major problem is to find a parameter representing this linearity: the determination coefficient $R^2$ obtained by linear regression is adapted to characterise it.

In a non-limiting example, the backscattered ultrasonic signal is divided into a number N of windows, said windows are averaged and the determination coefficient $R^2$ or the RMSE (designated Root Mean Squared Error) is calculated over these averages.

To do so, the signal s is divided into N windows of size M with $y_1$ corresponding to the average of the windows:

$$y_i = \frac{1}{M}\sum_{j=1}^{M} s(i,j)$$

$$i = [1, N]$$

A linear regression is then applied in the sense of the least squares: $y_i=ax_t+b$ with x the depth in millimeters. Linear regression consists in determining an estimation of the values a (highest degree coefficient) and b (y-intercept) and quantifying the validity of this relation using the determination coefficient $R^2$. The determination coefficient $R^2$ is comprised between 0 and 1. The closer it is to 1, the better the overall quality of the linear regression. It takes account of the linearity of the points $y_i$. If the points $y_i$ are perfectly aligned, the linear model will have a coefficient of determination $R^2$ equal to 1. Conversely, if the points are very dispersed, the deviation of the points from the straight line of the linear model will be important. The determination coefficient will tend towards 0.

The determination coefficient $R^2$ is calculated via the following formula:

$$R^2 = 1 - \frac{SCR}{SCT}$$

With:

$$SCR = \sum_{i}(y_i - \hat{y}_i)^2 = \text{the sum of the residual squares}$$

-continued $$SCT = \sum_{i}(y_i - \bar{y}_i)^2 = \text{the sum of the total squares}$$

In a non-limiting example, the coefficient RMSE is calculated via the following formula:

$$RMSE = \frac{1}{N}SCR$$

During a fourth step, a predictive value P of the presence of an acoustic signature of target biological tissue is calculated 104, the predictive value P being calculated via a statistical law using the at least two calculated instantaneous parameters, namely:
  the energy E of the backscattered ultrasonic signal,
  the attenuation ATT of the backscattered ultrasonic signal,
  the linearity LIN of the envelope of the backscattered ultrasonic signal.

In a non-limiting example, the statistical law is a logistic regression. According to one possibility, the predictive value P is calculated via the following logistic regression model:

$P=\beta_0+\beta_1 \cdot$Parameter_calculated_1+. . .
  $+\beta_n \cdot$Parameter_calculated_$n$ In the example described, the predictive value P is calculated via the following logistic regression model:

$P=\beta_0+\beta_1 \cdot$Parameter_calculated_1+
  $\beta_2 \cdot$Parameter_calculated_2+
  $\beta_3 \cdot$Parameter_calculated_3

With:
  Parameter_calculated_1=energy E of the backscattered ultrasonic signal,
  Parameter_calculated_2=attenuation ATT of the backscattered ultrasonic signal, and
  Parameter_calculated_3=linearity LIN of the envelope of the backscattered ultrasonic signal.

In a different embodiment, the calculation 104 of the predictive value P is carried out via the at least two calculated instantaneous parameters and calculated instantaneous parameters memorised earlier. During this implementation, calculated instantaneous parameters are memorised over a given time period.

For example:
  at moment T−2, the instantaneous parameters of the energy E and the linearity LIN are calculated and memorised;
  at moment T−1, the instantaneous parameters of the energy E and the linearity LIN are calculated and memorised;
  at moment T, the instantaneous parameters of the energy E and the linearity LIN are calculated.

According to this embodiment, the predictive value P is then calculated via the instantaneous parameters calculated and memorised at moment T−2 and at moment T−1 and the instantaneous parameters calculated at moment T. This particularity makes it possible to take into consideration the movements of biological tissues due for example to respiratory movements.

In a different embodiment, the calculation 104 of the predictive value calls on an instantaneous parameter calculated from the ultrasound signal obtained at different moments. This is the case for example when the inter-correlation coefficient between the ultrasound signals at moments T and T−1 is retained in the instantaneous parameters used for the calculation of the predictive value.

In a fifth step, one estimates 105 the probability that the target biological tissue is opposite the ultrasonic transducer 2, the estimation 105 depending on said calculated predictive value P and/or on at least one strength condition based on at least one of the two calculated instantaneous parameters E, LIN, ATT.

More particularly, the estimation 105 depending on the calculated predictive value P is carried out by comparing the calculated predictive value P with a single or several determined prediction threshold values such that: when the calculated predictive value P is compared to a single determined maximum prediction threshold value $S_{Max}$, then
- if the calculated predictive value P is strictly less than the determined maximum prediction threshold value $S_{Max}$ then the ultrasonic transducer 2 is opposite the target biological tissue,
- if the calculated predictive value P is greater than or equal to the determined maximum prediction threshold value $S_{Max}$, then the ultrasonic transducer 2 is opposite biological tissue different to the target biological tissue;

when the calculated predictive value P is compared to a determined maximum prediction threshold value $S_{Max}$ and a determined minimum prediction threshold value $S_{Min}$, then
- if the calculated predictive value P is less than or equal to the determined minimum prediction threshold value $S_{Min}$ then the ultrasonic transducer 2 is opposite the target biological tissue,
- if the calculated predictive value P is greater than or equal to the determined maximum prediction threshold value $S_{Max}$, then the ultrasonic transducer 2 is opposite biological tissue different to the target biological tissue,
- if the calculated predictive value P is strictly greater than the determined minimum prediction threshold value $S_{Min}$ and strictly less than the determined maximum prediction threshold value $S_{Max}$ then the ultrasonic transducer 2 is assumed to be opposite the target biological tissue. This uncertainty may correspond to an acoustic signature of the target biological tissue modified by the presence of heterogeneities caused by metastases or instead by the presence of blood vessels, etc.

It should be noted that for a same biological tissue such as for example the hepatic parenchyma, depending on the ultrasonic frequencies transmitted by the ultrasonic transducer 2, the minimum $S_{Min}$ and maximum $S_{Max}$ prediction threshold values used differ.

During the fifth step, it is also possible to estimate 105, depending on at least one strength condition based on at least one of the two calculated instantaneous parameters E, LIN, ATT, the probability that the target biological tissue is opposite the ultrasonic transducer 2.

More particularly, the at least one strength condition may be:
- if the linearity LIN of the envelope of the calculated backscattered ultrasonic signal is greater than or equal to a determined threshold linearity value $S_{Lin}$, then the ultrasonic transducer 2 is opposite the target biological tissue, and/or
- if the energy E of the backscattered ultrasonic signal is greater than or equal to a determined threshold energy value $E_{Min}$, then the ultrasonic transducer 2 is opposite the target biological tissue.

In a non-limiting example and as indicated previously, the representative value of the linearity LIN of the envelope of the calculated backscattered ultrasonic signal may be the determination coefficient $R^2$.

On the other hand, whatever the calculated predictive value P:
- if the linearity LIN of the envelope of the calculated backscattered ultrasonic signal is strictly less than the determined threshold linearity value $S_{Lin}$, then the ultrasonic transducer 2 is opposite biological tissue different to the target biological tissue,
- if the energy E of the backscattered ultrasonic signal is strictly less than the determined threshold energy value $E_{min}$, then the ultrasonic transducer 2 is opposite biological tissue different to the target biological tissue.

Thus, it should be noted that if at least one of the strength conditions indicates that the ultrasonic transducer 2 is not situated opposite the target biological tissue then the calculated predictive value P is not taken into account. In other words, if at least one of the strength conditions indicates that the ultrasonic transducer 2 is not situated opposite the target biological tissue then the estimation depending on the calculated predictive value P is not taken into consideration during the estimation 105.

As an example, the estimation 105 depending on at least one strength condition based on the linearity LIN of the backscattered ultrasonic signal makes it possible to verify that there is no important heterogeneity such as for example the presence of vessels and also to verify that the hepatic parenchyma is situated opposite the ultrasonic transducer.

As an example, the estimation 105 depending on at least one strength condition based on the energy E of the backscattered ultrasonic signal makes it possible to verify that the ultrasonic transducer 2 is correctly coupled to the studied medium or that it is not situated opposite a hard part (bone). When the ultrasonic transducer 2 is not coupled correctly with the medium (ultrasonic transducer in contact with a bone or not in contact), the energy E of the backscattered ultrasonic signal is very low.

It should be noted that the determined minimum threshold energy value $E_{Min}$ and the determined minimum threshold linearity value $S_{Lin}$ are determined empirically by data analysis.

It should be noted that for a same biological tissue such as for example the hepatic parenchyma, depending on the ultrasonic frequencies transmitted by the ultrasonic transducer 2, the determined minimum threshold energy value $E_{Min}$ and the determined minimum threshold linearity value $S_{Lin}$ used differ.

Thus, the determined minimum threshold energy value $E_{Min}$ and the determined minimum threshold linearity value $S_{Lin}$ used in the strength conditions for an ultrasonic transducer 2 transmitting an ultrasound frequency of 2.5 MHz will be different from a minimum threshold energy value $E_{min}$ and from a minimum threshold linearity value $S_{Lin}$ used in the strength conditions for an ultrasonic transducer 2 transmitting an ultrasound frequency of 3.5 MHz.

In an implementation of the invention, the method comprises an additional step of indicating 106 in real time the probability that the target biological tissue is opposite the ultrasonic transducer 2.

The indication 106 may be visual and/or audible and/or tactile. The visual indication may be a parametric indication (in other words in the form of a numerical value) or colorimetric. The audible indication may be by means of a ringing beep when the ultrasonic transducer 2 is not situated opposite the target biological tissue, or vice versa.

In a non-limiting example, when the indication 106 is visual, the indicator making it possible to indicate the probability that the target biological tissue is opposite the ultrasonic transducer 2 may be represented in the form of a red—orange—green traffic light:
- the colour red indicating that the ultrasonic transducer 2 is not situated opposite the target biological tissue,
- the colour orange indicating that the ultrasonic transducer 2 is probably situated opposite the target biological tissue, in this case a quantitative and/or qualitative measurement 107 of the target biological tissue may be triggered automatically or manually by an operator,
- the colour green indicating that the ultrasonic transducer 2 is situated opposite the target biological tissue, in this case a quantitative and/or qualitative measurement 107 of the target biological tissue may be triggered automatically or manually by an operator.

Thanks to this indication 106, the colour varies in real time depending on the movement of the ultrasonic transducer 2. The indication 106 thus makes it possible to determine whether the ultrasonic transducer 2 is situated opposite biological tissue.

In a different implementation of the invention illustrated in FIG. 3, the visual indication 106 is realised by the display of a colour gradient, to be specific the colour grey. Preferentially, the colour gradient is of green colour. The green colour gradient makes it possible to obtain a multitude of different green colours varying as a function of the biological tissue situated opposite the ultrasonic transducer 2. As an example, if the display colour is light green then the ultrasonic transducer 2 is situated opposite the target biological tissue. Conversely, if the display colour is dark green or even black then the ultrasonic transducer 2 is situated opposite biological tissue different to the target biological tissue.

Such a colour gradient may for example follow an S-shaped curve, subject to a transparency law of type:

$$y = 1 - [1/(1+e^{-x})] \text{ with } x = P\text{estimated\_}105 + S_{Min}$$

In this equation:
- when the at least one strength condition is not taken into consideration during the step of estimating 105 the probability that the target biological tissue is opposite the ultrasonic transducer 2 then $P_{estimated\_105}$=predictive value P calculated during step 104,
- when the at least one strength condition is taken into consideration during the step of estimating 105 the probability that the target biological tissue is opposite the ultrasonic transducer 2 then $P_{estimated\_105}$ takes account of the predictive value P calculated during step 104 and one at least of the two calculated instantaneous parameters, namely in the example described the determination coefficient $R^2$ (or linearity LIN of the backscattered ultrasonic signal) and the energy E of the backscattered ultrasonic signal. If at least one of the two parameters indicates that the ultrasonic transducer is not situated opposite the target biological tissue then $P_{estimated\_105}$ is considered as being equal to the prediction maximum threshold value $S_{max}$.

This hypothesis indicates that the ultrasonic transducer 2 is not situated opposite the target biological tissue.

In FIG. 3, the x-axis represents the estimation of the probability $P_{estimated\_105}$ that the target biological tissue is opposite said ultrasonic transducer (x of the transparency law) and the y-axis represents "y" of the transparency law.

This transparency law has the objective of adapting the transition between an opaque colour (for example opaque grey in FIG. 3 or according to another example not represented opaque green) and the same colour but transparent (for example, transparent grey or transparent green). The slope of this curve is the transition zone between the opaque colour and the transparent colour. This transition zone may be adapted according to the compromise between the presence of the target biological tissue called optimal from the presence of biological tissue called intermediate depending on what is sought. Optimal is taken to mean a high probability of being opposite the target biological tissue. Intermediate is taken to mean the lower average probability of being opposite the target biological tissue.

To summarise, in the example described, the greater the transparency the lighter the colour. Conversely, the lower the transparency, the darker the colour. It is understood that the colour green or the colour grey are not limiting.

As an example, for an estimation value $P_{estimated\_105}$ of the probability that the target biological tissue is opposite said ultrasonic transducer equal to 1.8, the corresponding transparency y is equal to 0.2. Since the value y of the transparency is low, the indication colour 106 obtained represented on the indicator 5 is dark.

By analogy with the preceding indication example 106, opaque green corresponds to the green light, transition green to the orange light and transparent green to the red light.

Such an indication is understandable by the majority of the population without requiring enhanced knowledge in the field of medicine. In fact, when the operator perceives a green colour, he knows that the ultrasonic transducer 2 is situated opposite the target biological tissue.

As indicated previously, the method 100 also comprises a quantitative and/or qualitative measurement step (MEAS) 107 of the target biological tissue, this measurement 107 being able to be triggered automatically or manually by an operator when the indication 106 indicates that the ultrasonic transducer 2 is situated opposite the target biological tissue. In the case of the liver, the measurement 107 is carried out, for example, over a depth PF comprised between 25 mm and 80 mm, the depth PF being measured from the contact surface between said ultrasonic transducer 2 and the biological tissue in contact. For example, the depth PF may be comprised between:
- 35 and 75 mm for a transmitting frequency of the order of 2.5 MHz,
- 25 and 65 mm for a transmitting frequency of the order of 3.5 MHz, or
- 15 and 55 mm for a transmitting frequency of the order of 6 MHz.

During this step, it is possible to measure the elasticity of the biological tissues, the viscosity of the biological tissues, the CAP (Controlled Attenuation Parameter) or any other quantitative parameter derived from ultrasonic signals characterising soft biological tissues.

The method 100 also comprises a step of validation (VALID_MEAS) 108 of the quantitative and/or qualitative measurement 107. This validation step 108 makes it possible to ensure that the measurement obtained is a measurement representative of the target biological tissue.

Generally speaking, the method 100 of the invention makes it possible in particular to:
- determine, in real time, whether the ultrasonic transducer is positioned opposite target biological tissue,
- quantify the quality of the ultrasonic signal backscattered by the biological tissue,
- carry out a 2D (two dimensions) or 3D (3 dimensions) measurement and, more advantageously, uniquely in 1D (one dimension), in other words on one ultrasonic line: in fact a 2D or 3D measurement is not necessary, consequently the processing of the data of the backscattered ultrasonic signal is quicker, considering the sensitivity and the frequency of ultrasonic transducers, in other words that for a specific ultrasonic transducer the sensitivity and the frequency of the specific ultrasonic transducer supplied by the manufacturer are taken into consideration so as to adapt the signal transmitted by said specific ultrasonic transducer to the statistical law;

detecting an error due to the operator for example a lack of ultrasonic couplant or ultrasonic gel (weak ultrasonic signal);

detecting a technical failure for example a connectivity problem generating a loss of ultrasonic signal;

to be used as a criterion for validation of a measurement or confidence index on the measurement carried out.

The method 100 of the invention has more particularly been described in the case of an application to the hepatic parenchyma (or liver). Nevertheless, it is understood that such a method may be applied to any type of biological tissue. To do so, it is necessary to recalculate the relevant coefficients and thresholds values vis-à-vis this new target biological tissue.

The invention also relates to a device 1 (Cf. FIG. 1) for determining, in real time, the probability that target biological tissue 6 is opposite an ultrasonic transducer 2.

As indicated previously, the device 1 comprises an ultrasonic transducer 2 connected to an information processing unit 3 by a wire link 4. The device 1 further comprises an indicator 5 in real time of the probability that target biological tissue is opposite the ultrasonic transducer 2.

The device 1 is capable of:
transmitting 101, via the ultrasonic transducer 2, an ultrasonic signal into biological tissue;
receiving 102, via the ultrasonic transducer 2, the transmitted ultrasonic signal which is backscattered by the biological tissue;
calculating 103 at least two instantaneous parameters E, LIN, ATT of the backscattered ultrasonic signal;
calculating 104 a predictive value P of the presence of an acoustic signature of the target biological tissue, the predictive value P being calculated via a statistical law using the at least two calculated instantaneous parameters E, LIN, ATT;
estimating 105 the probability that the target biological tissue is opposite the ultrasonic transducer 2, the estimation 105 depending on the predictive value P and/or on at least one strength condition based on at least one of the two calculated instantaneous parameters E, LIN, ATT,
indicating 106, via an indicator 5, in real time the probability that the target biological tissue is opposite the ultrasonic transducer 2.

The indicator 5 makes it possible to indicate in real time to the operator using the device 1 if the ultrasonic transducer 2 is positioned opposite the target biological tissue. Thus, the use of such a device 1 does not require any competence in the medical field or even in medical instrumentation. As indicated previously, the indicator 5 may be in the form of a traffic light, a colour gradient, a colour subjected to a transparency law or instead a colour range (i.e. colour palette).

Moreover, the device 1 for determining in real time the probability that target biological tissue 6 is opposite an ultrasonic transducer 2 may be an elastograph, an echograph or more generally any device using ultrasounds. Thus, such a device 1 not only makes it possible to position the ultrasonic transducer 2 opposite the target biological tissue but also to carry out a quantitative and/or qualitative measurement of the target biological tissue.

The invention claimed is:

1. Method for determining, in real time, a probability that target biological tissue is opposite an ultrasonic transducer, said method comprising:
transmitting, via an ultrasonic transducer, at least one ultrasonic signal into a biological tissue;
receiving, via said ultrasonic transducer, at least one ultrasonic signal which has been backscattered by said biological tissue;
calculating at least two instantaneous parameters of said at least one backscattered ultrasonic signal;
calculating a predictive value of the presence of an acoustic signature of a target biological tissue, said predictive value being calculated via a statistical law using said at least two calculated instantaneous parameters; and
estimating a probability that said target biological tissue is opposite said ultrasonic transducer, said estimation depending on said calculated predictive value and on at least one strength condition based on at least one of said two calculated instantaneous parameters; and
triggering, based on the estimated probability, a quantitative measurement of said target biological tissue when said ultrasonic transducer is opposite said target biological tissue.

2. Method according to claim 1, wherein said calculation of a predictive value is carried out via said at least two calculated instantaneous parameters and previously calculated parameters.

3. Method according to claim 1, wherein said estimation depending on said calculated predictive value is carried out by comparing said calculated predictive value with a single or several prediction threshold values determined such that:
when the calculated predictive value is compared to a single determined maximum prediction threshold value,
if the calculated predictive value is less than the determined maximum prediction threshold value, then the ultrasonic transducer is opposite the target biological tissue, and
if the calculated predictive value is greater than or equal to the determined maximum prediction threshold value, then the ultrasonic transducer is opposite biological tissue different to the target biological tissue; and
when the calculated predictive value is compared to the determined maximum prediction threshold value and a determined minimum prediction threshold value,
if the calculated predictive value is less than or equal to the determined minimum prediction threshold value, then the ultrasonic transducer is opposite the target biological tissue,
if the calculated predictive value is greater than or equal to the determined maximum prediction threshold value, then the ultrasonic transducer is opposite biological tissue different to the target biological tissue, and
if the calculated predictive value is greater than the determined minimum prediction threshold value and less than the determined maximum prediction threshold value, then the ultrasonic transducer is opposite the target biological tissue.

4. Method according to claim 1, wherein said at least two calculated instantaneous parameters are chosen from the following parameters:
- an energy of said at least one backscattered ultrasonic signal,
- an attenuation of said at least one backscattered ultrasonic signal,
- a linearity of an envelope of said at least one backscattered ultrasonic signal.

5. Method according to claim 4, wherein said strength condition is:
- if the linearity of the envelope of said at least one calculated backscattered ultrasonic signal is greater than or equal to a determined linearity threshold value, then said ultrasonic transducer is opposite said target biological tissue, and/or
- if the energy of said at least one backscattered ultrasonic signal is greater than or equal to a determined threshold energy value, then said ultrasonic transducer is opposite said target biological tissue.

6. Method according to claim 4, wherein whatever said calculated predictive value, said strength condition is:
- if said linearity of the envelope of said at least one calculated backscattered ultrasonic signal is less than a determined linearity threshold value, then said ultrasonic transducer is opposite biological tissue different to said target biological tissue,
- if said energy of said at least one backscattered ultrasonic signal is less than a determined threshold energy value, then said ultrasonic transducer is opposite biological tissue different to said target biological tissue.

7. Method according to claim 1, wherein said statistical law is a logistic regression such that said predictive value is calculated via said following logistic regression:

$$P=\beta_0+\beta_1 \cdot \text{Parameter\_calculated\_1}+\ldots +\beta_n \cdot \text{Parameter\_calculated\_}n$$

wherein P is the predictive value, and $\beta_0, \beta_1 \ldots \beta_n$ are coefficients.

8. Method according to claim 1, comprising indicating in real time the probability that target biological tissue is opposite said ultrasonic transducer.

9. Method according to claim 8, wherein said indication is an indication that is:
- visual, and/or
- audible and/or
- tactile.

10. Method according to claim 9, wherein said visual indication is realised by a display of a colour gradient, a first colour in the colour gradient indicating that said ultrasonic transducer is not situated opposite said target biological tissue, and a second colour in the colour gradient different than the first colour indicating that said ultrasonic transducer is situated opposite said target biological tissue.

11. Method according to claim 10, wherein said colour gradient follows an S-shaped curve.

12. Method according to claim 10, wherein a third colour in the colour gradient intermediate the first and second colours indicates a probability that said ultrasonic transducer is situated opposite said target biological tissue by being closer to either the first or second colour in the gradient.

13. Method according to claim 1, wherein the triggering is automatic or manual.

14. Method according to claim 13, wherein the triggered measurement is carried out over a determined depth depending on the frequency of said at least one transmitted ultrasonic signal, said depth being measured from the contact surface between said ultrasonic transducer and said biological tissue in contact to a point within said biological tissue from which the at least one backscattered ultrasonic signal is received via said ultrasonic transducer.

15. Method according to claim 13, comprising validating said quantitative measurement, wherein the validation is carried out via said calculated predictive value.

16. Device for determining, in real time, a probability that target biological tissue is opposite an ultrasonic transducer, said device comprising:
- at least one ultrasonic transducer configured to transmit and receive ultrasound signals; and
- a processor configured to perform the steps of:
  - causing said ultrasonic transducer to transmit at least one ultrasonic signal into a biological tissue;
  - causing said ultrasonic transducer to receive at least one ultrasonic signal which has been backscattered by said biological tissue;
  - calculating at least two instantaneous parameters of said at least one backscattered ultrasonic signal;
  - calculating a predictive value of the presence of an acoustic signature of a target biological tissue, said predictive value being calculated via a statistical law using said at least two calculated instantaneous parameters;
  - estimating a probability that said target biological tissue is opposite said ultrasonic transducer, said estimation depending on said predictive value and at least one strength condition based on at least one of said two calculated instantaneous parameters; and
  - indicating, via an indicator, in real time, the probability that said target biological tissue is opposite said ultrasonic transducer; and
  - triggering, based on the estimated probability, a quantitative measurement of said target biological tissue when said ultrasonic transducer is opposite said target biological tissue.

17. Method for determining, in real time, a probability that target biological tissue is opposite an ultrasonic transducer, said method comprising:
- transmitting, via an ultrasonic transducer, at least one ultrasonic signal into a biological tissue;
- receiving, via said ultrasonic transducer, at least one ultrasonic signal which has been backscattered by said biological tissue;
- calculating at least two instantaneous parameters of said at least one backscattered ultrasonic signal, wherein a first parameter of said at least two calculated instantaneous parameters is a linearity of an envelope of said at least one backscattered ultrasonic signal;
- calculating a predictive value of the presence of an acoustic signature of a target biological tissue, said predictive value being calculated via a statistical law using said at least two calculated instantaneous parameters; and
- estimating a probability that said target biological tissue is opposite said ultrasonic transducer, said estimation depending on said calculated predictive value and/or on at least one strength condition based on at least the first parameter; and
- triggering, based on the estimated probability, a quantitative measurement of said target biological tissue when said ultrasonic transducer is opposite said target biological tissue.

* * * * *